US012765876B2

(12) United States Patent
Park

(10) Patent No.: US 12,765,876 B2
(45) Date of Patent: Oct. 20, 2026

(54) EGG-SHAPED STAPLER FOR INTESTINAL ANASTOMOSIS

(71) Applicant: KOREA UNIVERSITY RESEARCH AND BUSINESS FOUNDATION, Seoul (KR)

(72) Inventor: Sungsoo Park, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 502 days.

(21) Appl. No.: 17/925,319

(22) PCT Filed: Mar. 23, 2021

(86) PCT No.: PCT/KR2021/003565
§ 371 (c)(1),
(2) Date: Nov. 15, 2022

(87) PCT Pub. No.: WO2021/241867
PCT Pub. Date: Dec. 2, 2021

(65) Prior Publication Data

US 2023/0190273 A1 Jun. 22, 2023

(30) Foreign Application Priority Data

May 26, 2020 (KR) ........................ 10-2020-0062971

(51) Int. Cl.
*A61B 17/11* (2006.01)
*A61B 17/115* (2006.01)

(52) U.S. Cl.
CPC ......... *A61B 17/115* (2013.01); *A61B 17/1114* (2013.01); *A61B 2017/1132* (2013.01)

(58) Field of Classification Search
CPC ............... A61B 17/115; A61B 17/1114; A61B 2017/1132
See application file for complete search history.

(56) References Cited

U.S. PATENT DOCUMENTS 4,304,236 A * 12/1981 Conta .................. A61B 17/115 227/19
4,473,077 A * 9/1984 Noiles .................. A61B 17/115 227/19

(Continued)

FOREIGN PATENT DOCUMENTS

CN 101011277 A 8/2007
CN 108618821 A 10/2018

(Continued)

OTHER PUBLICATIONS

International Search Report for PCT/KR2021/003565 mailed Aug. 27, 2021 from Korean Intellectual Property Office.

(Continued)

*Primary Examiner* — Alexander J Orkin
(74) *Attorney, Agent, or Firm* — Revolution IP, PLLC

(57) ABSTRACT

The present invention relates to an egg-shaped stapler for intestinal anastomosis, the stapler including: an anvil head having an oval bottom inner circumferential surface; a rear head which has an oval bottom inner circumferential surface that comes into contact with the bottom inner circumferential surface of the anvil head and which includes a staple receiving port for receiving a staple along the oval bottom inner circumferential surface thereof; and a handle part, one end of which is coupled to the rear head and the other end of which extends backwards so as to operate at least one of the anvil head and the rear head.

4 Claims, 5 Drawing Sheets

(56) References Cited

U.S. PATENT DOCUMENTS

| | | | | | |
|---|---|---|---|---|---|
| 4,700,703 | A * | 10/1987 | Resnick | A61B 17/115 | 227/176.1 |
| 4,752,024 | A * | 6/1988 | Green | A61B 17/115 | 606/220 |
| 4,817,847 | A * | 4/1989 | Redtenbacher | A61B 17/1155 | 227/19 |
| 5,197,649 | A | 3/1993 | Bessler et al. | | |
| 5,330,486 | A * | 7/1994 | Wilk | A61B 17/115 | 227/181.1 |
| 5,411,508 | A * | 5/1995 | Bessler | A61B 17/1114 | 227/19 |
| 5,588,579 | A * | 12/1996 | Schnut | A61B 17/115 | 227/19 |
| 5,695,504 | A * | 12/1997 | Gifford, III | A61B 17/12045 | 606/139 |
| 5,709,335 | A * | 1/1998 | Heck | A61B 17/115 | 227/176.1 |
| 5,732,872 | A * | 3/1998 | Bolduc | A61B 17/0644 | 227/176.1 |
| 6,605,078 | B2 * | 8/2003 | Adams | A61B 90/30 | 606/1 |
| 10,070,866 | B1 * | 9/2018 | Kellerman | A61B 17/1155 | |
| 2003/0018236 | A1 * | 1/2003 | Adams | A61B 1/00071 | 600/128 |
| 2003/0144675 | A1 | 7/2003 | Nicolo | | |
| 2003/0178465 | A1 * | 9/2003 | Bilotti | A61B 17/115 | 227/180.1 |
| 2007/0175963 | A1 * | 8/2007 | Bilotti | A61B 17/115 | 227/179.1 |
| 2009/0078736 | A1 | 3/2009 | Van Lue | | |
| 2011/0017800 | A1 * | 1/2011 | Viola | A61B 17/115 | 227/175.1 |
| 2013/0175318 | A1 * | 7/2013 | Felder | A61B 17/115 | 227/175.1 |
| 2014/0191012 | A1 | 7/2014 | Chen et al. | | |

FOREIGN PATENT DOCUMENTS

| | | | |
|---|---|---|---|
| EP | 2277459 | B1 | 3/2016 |
| KR | 10-2008-0021527 | A | 3/2008 |
| KR | 10-2019-0028164 | A | 3/2019 |

OTHER PUBLICATIONS

Xu, et al., "A Novel Spherical Magnetic Compression Device for Colorectal Anastomosis in a Swine Model", Journal of Laparoendoscopic & Advanced Surgical Techniques, 2015, vol. 25, No. 4, pp. 323-329.

Office Action of Chinese Patent Application No. 202180037692.5 dated Mar. 10, 2025.

* cited by examiner

Prior Art

Prior Art

EGG-SHAPED STAPLER FOR INTESTINAL ANASTOMOSIS

TECHNICAL FIELD

The present invention relates to an egg-shaped stapler for intestinal anastomosis, and more particularly, to an egg-shaped stapler for intestinal anastomosis in which, in a state in which an anvil head and a rear head are coupled along an insertion direction in an intestine, since the anvil head and the rear head are formed in an egg-like shape, it is possible to be safely and conveniently insert the anvil head and the rear head into the intestine, after insertion, it is possible to conveniently and accurately couple the anvil head and the rear head through a magnetic coupling, and even when an inner diameter of the intestine is small, it is possible to enlarge an area of an inner diameter of an anastomosis part formed after suturing.

BACKGROUND ART

This section provides background information related to the present invention which is not necessarily related art Anastomosis refers to joint surgery performed in cases of esophageal reconstruction after surgery to partially remove an esophagus due to an esophageal cancer in the human body, a junction of an esophagus and a duodenum after surgery to remove a stomach due to a gastric cancer, large intestine reconstruction after surgery to partially remove a large intestine due to a colorectal disease such as a colorectal cancer, and rectal reconstruction after surgery to remove a lesion in a rectum. Until recently, simple anastomosis through classical manual suture has been performed, and anastomosis is still one of the most frequently performed medical procedures. However, in case of such manual suture, after suture surgery, complications due to leakage of an anastomosis part and the secondary changes resulting therefrom cause stenosis of the anastomosis part in many cases, which is recognized as an important factor affecting the prognosis of a patient. In order to solve such problems, a circular stapler as a surgical tool used for a surgical operation of a tubular organ is widely used in such anastomosis surgery.

FIG. 1 is an image of a conventional circular stapler, and FIG. 2 is a view illustrating an example of a circular stapler disclosed in Korean Patent Publication No. 10-2019-0028164. For convenience of description, some of the drawing symbols are changed.

A circular stapler 10 includes three parts including a head part 20, a connection part 30, and a handle part 40. The head part 20 is a part that performs a function of anastomosing an intestine through a stapler during surgery and cutting unnecessary soft tissues. The connection part 30 is a connection part formed in a shape that may be deformed according to a shape of an intestine or a surgical site during surgery. The handle part 40 is a part that controls the interface pressure of intestinal soft tissue during anastomosis, fires staples for anastomosis, and generates mechanical power for cutting soft tissue.

The head part 20 includes a rear head 21 which accommodates the staples therein and fires the staple using a driving force provided by a driving part (not shown) and an anvil head 22 provided with an anvil 23*b* which is coupled to a leading end of the rear head 21 to guide the fired staple to be bent. A trocar 24 may be provided at the leading end of the rear head 21, and an anvil shaft 25 coupled to the trocar 24 may be provided at a rear end of the anvil head 22.

However, since the conventional circular stapler 10 includes the anvil shaft 25, which is called a sharply protruding trocar, and the trocar 24, when the circular stapler 10 is inserted into an intestine, the circular stapler 10 may damage the intestine, which is very inconvenient. For example, referring to FIG. 3 conceptually illustrating a problem of the circular stapler 10, in the conventional circular stapler 10, in order to secure a sufficient area of an anastomosis part after intestinal anastomosis, the anvil head 22 should be inserted into an intestine in a state perpendicular to a dotted line 31 corresponding to a circular cross section of an intestine 30, and thus intestinal damage often occurs when a sufficient intestinal diameter is not secured. In the conventional circular stapler 10, since the sharply protruding anvil shaft 25 and the trocar 24 should be aligned and coupled according to a straight line 32 in a perfectly parallel plane, it is not easy to accurately align and couple the anvil shaft 25 and the trocar 24 along the straight line 32 during surgery using a laparoscope. For convenience of description, the anvil head 22, the rear head 21, and the intestine 30 are schematically illustrated in a conceptual view of FIG. 3. Furthermore, in the conventional circular stapler 10, since the anvil 23, which guides the fired staple to be bent, has a circular shape, an area of a sutured inner diameter varies according to a size of an inner diameter of an intestine, and in this case, there is a problem in that a risk of stenosis is increased when the size of the inner diameter of the intestine is small.

The present invention is directed to providing a stapler which does not include a sharply protruding anvil shaft and a trocar and includes an anvil head having an oval-shaped anvil.

DISCLOSURE

Technical Problem

The problems to be solved by the present disclosure will be described in the latter part of the modes of the invention.

Technical Solution

This section provides a general summary of the present invention and is not a comprehensive disclosure of its full scope or all of its features.

According to an aspect of the present invention, there is provided an egg-shaped stapler for intestinal anastomosis including an anvil head which has a bottom inner circumferential surface having an oval shape, a rear head which has a bottom inner circumferential surface having an oval shape in contact with the bottom inner circumferential surface of the anvil head and includes staple accommodation holes configured to accommodate staples along the oval bottom inner circumferential surface, and a handle part which has one end portion coupled to the rear head and the other end portion extending in a rear direction and operates at least one of the anvil head and the rear head.

Advantageous Effects

The advantageous effects of the present disclosure will be described in the latter part of in the latter part of the modes of the Invention.

MODES OF THE INVENTION

Hereinafter, the present invention will be described in detail with reference to the accompanying drawings. Also, in this specification, direction indications such as up/down, up/down, and the like are based on the drawings.

Hereinafter, exemplary embodiments of the present invention will be described in detail with reference to the accompanying drawings. In this case, the same reference numbers are used throughout the drawings to refer to the same or like parts. Detailed descriptions of well-known functions and configurations which may obscure the gist of the present invention will be omitted. For the same reason, some of the elements in the accompanying drawings are exaggerated, omitted, or schematically illustrated.

Throughout the specification, when a portion may "comprise" or "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

Figure 4:
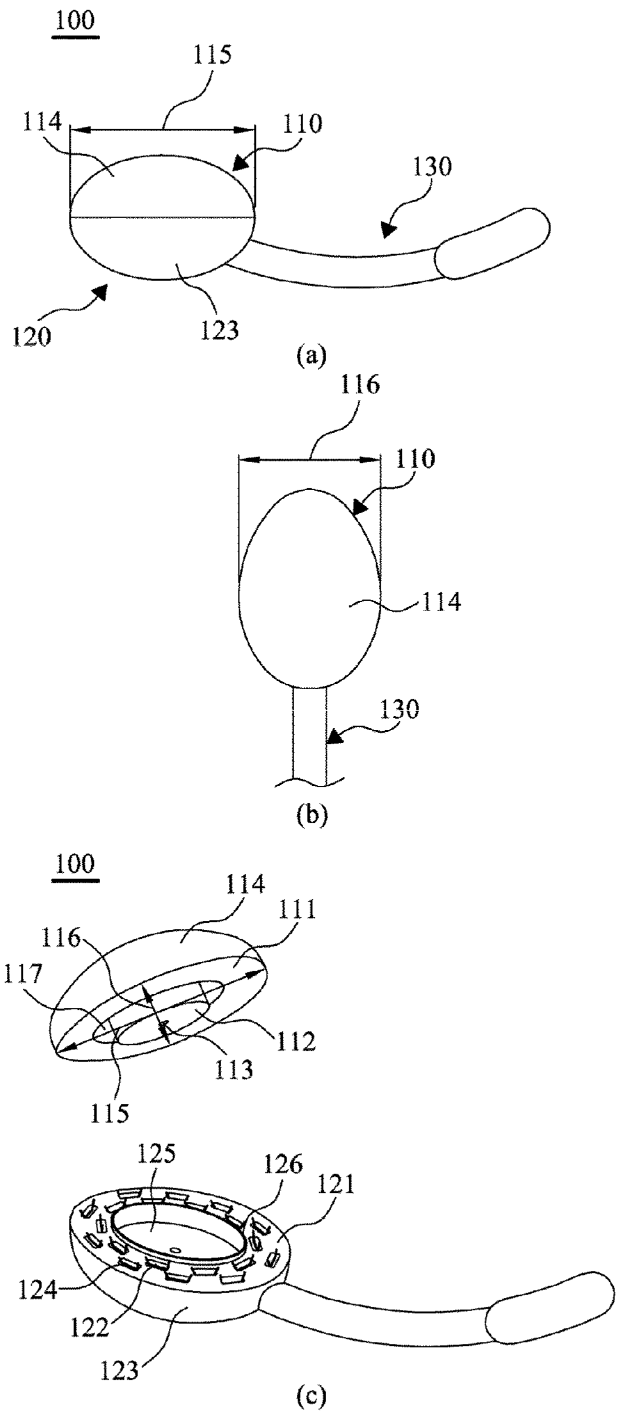
FIG. 4 shows perspective views illustrating an example of an egg-shaped stapler for intestinal anastomosis.

FIG. 4 shows perspective views illustrating an example of an egg-shaped stapler for intestinal anastomosis. FIGS. 4A and 4B are perspective views illustrating a state in which an anvil head 110 and a rear head 120 are combined, and FIG. 4C is a perspective view illustrating a state in which the anvil head 110 and the rear head 120 are separated.

Figure 5:
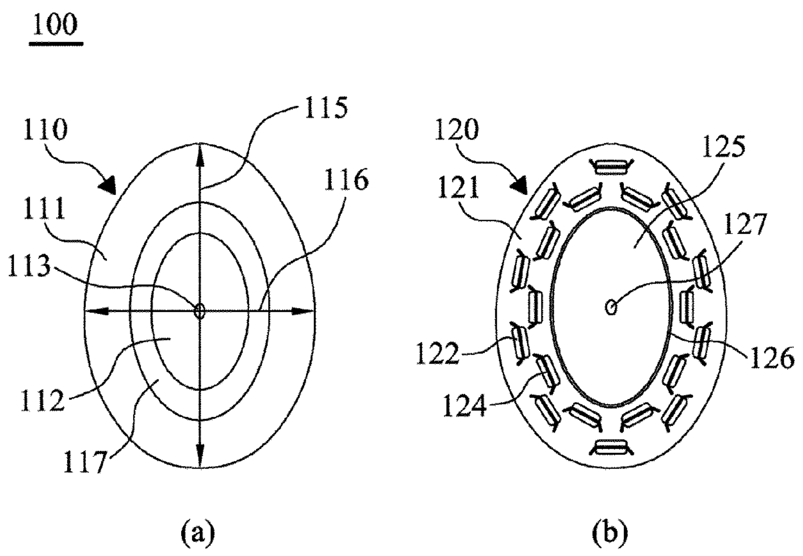
FIG. 5 shows plan views illustrating an example of surfaces on which an anvil head and a rear head of the egg-shaped stapler for intestinal anastomosis are coupled according to the present invention.

FIG. 5 shows plan views illustrating an example of surfaces on which the anvil head 110 and the rear head 120 of an egg-shaped stapler 100 for intestinal anastomosis according to the present invention are coupled.

Descriptions will be provided with reference to FIGS. 4 and 5.

Figure 1:
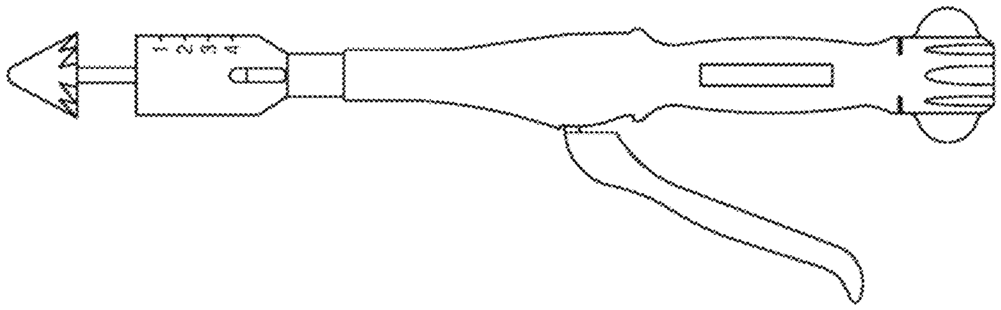
FIG. 1 is an image of a conventional circular stapler.
Figure 2:
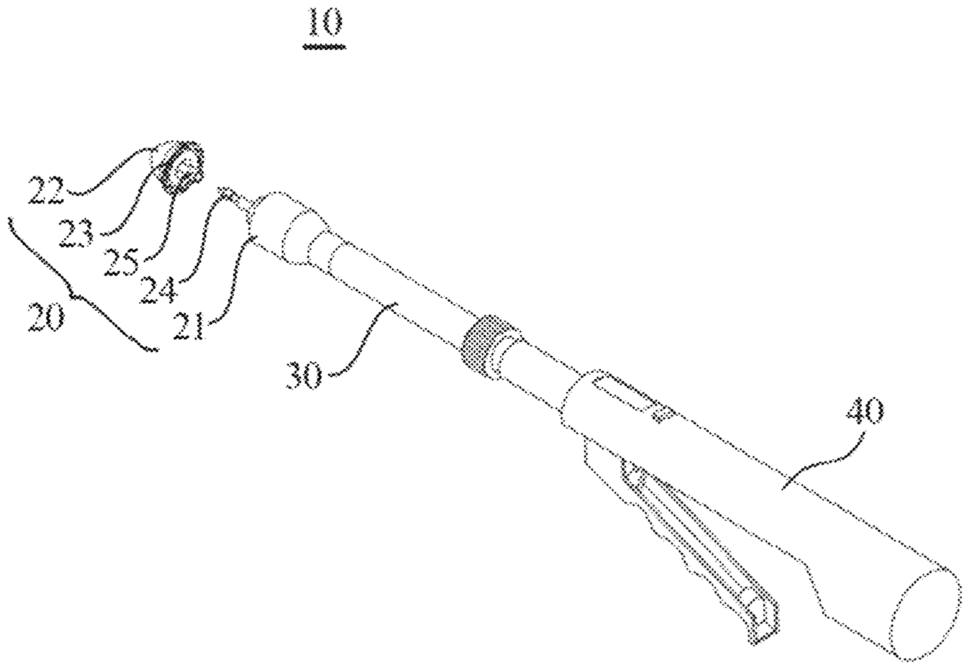
Prior Art FIG. 2
FIG. 2 is a view illustrating an example of a circular stapler disclosed in Korean Patent Publication No. 10-2019-0028164.
Figure 3:
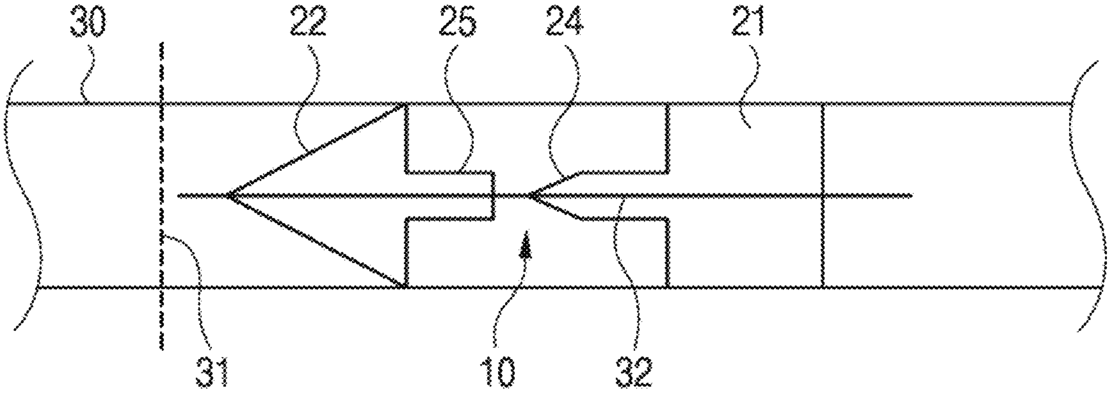
FIG. 3 is a conceptual view illustrating a problem of a conventional circular stapler.

The egg-shaped stapler 100 for intestinal anastomosis includes the anvil head 110, the rear head 120, and a handle part 130. That is, the egg-shaped stapler 100 for intestinal anastomosis includes the anvil head 110, the rear head 120, and the handle part 130 in which, unlike an anvil head shown in FIGS. 1 and 2 which forms an anastomosis shape as a circular shape, since the anvil head 110 and the rear head 120 to be described below are formed in a flat oval shape in an insertion direction, it is possible to easily insert the anvil head 110 and the rear head 120 into an intestine, and even when an inner diameter of the intestine is small, it is possible to enlarge an area of a sutured inner diameter of an anastomosis part formed after suturing.

The anvil head 110 has a bottom inner circumferential surface 111 corresponding to an anvil for guiding a fired staple to be bent. Unlike an anvil 23 of a conventional anvil head 22, the bottom inner circumferential surface 111 may be formed in an oval shape rather than a circular shape. An advantage of a case in which the bottom inner circumferential surface 111 is formed in an oval shape rather than a circular shape will be described with reference to FIG. 7 again. The bottom inner circumferential surface 111 may be provided with a magnet. The magnet may be formed as a neodymium magnet. The magnet may be formed as an electromagnet, and when the electromagnet needs to be attached to or detached from the rear head 120 in an intestine, magnetism is imparted to or released from the electromagnet to induce the electromagnet to be coupled to the rear head 120. A shape of the magnet may be formed as an oval donut shape to correspond to a shape of the bottom inner circumferential surface 111. However, the shape is not limited to the donut shape, and a plurality of magnets may be arranged at equal intervals in a circumferential direction.

The anvil head 110 may further include a coupling guide 112. The coupling guide 112 is formed to protrude from the bottom inner circumferential surface 111 inside the bottom inner circumferential surface 111, thereby further facilitating a coupling between the anvil head 110 and the rear head 120. Unlike a pointed anvil shaft 24 provided in the conventional anvil head 22, the coupling guide 112 of the present invention protrudes to be wide and flat, thereby reducing damage to an intestine when the anvil head 110 is inserted into the intestine. A trocar accommodation groove 113 capable of guiding and accommodating a trocar 127 fired to protrude from the rear head 120 may be provided inside the coupling guide 112 of the anvil head 110.

A surface 114 opposite to the bottom inner circumferential surface 111 of the anvil head 110, that is, the surface 114 facing in an insertion direction in an intestine may be formed in a flat hemispherical shape, and the bottom inner circumferential surface 111 may be flat and formed to be inclined at a certain angle with respect to the insertion direction. The anvil head 110 is formed in an oval shape in which a length of a major axis 115 is different from a length of a minor axis 116. That is, the anvil head 110 is formed in an oval shape having a diameter that is relatively greater than an inner diameter of an intestine, and an oval cross section is formed to have a major axis in a direction from an upper side toward a lower side thereof and concurrently is formed in a flat hemisphere shape like an egg in an insertion direction of the anvil head 110.

As described above, when a shape of the anvil head 110 is formed as an elongated hemispherical shape similar to an egg rather than a perfect hemispherical shape, smooth insertion is guided by offsetting a risk of, when the anvil head 110 is pushed into an intestine, damaging the intestine due to an insufficient inner diameter of the intestine. Since a leading end of a conventional anvil head 110 is formed as a pointed end has a narrow diameter, it is impossible to solve the above-described features of the present invention.

The rear head 120 has a flat bottom inner circumferential surface 121 in contact with the bottom inner circumferential surface 111 of the anvil head 110, and staple accommodation holes 122 capable of accommodating staples 124 are formed in the bottom inner circumferential surface 121. A surface 123 opposite to the bottom inner circumferential surface 121 is formed in a flat hemispherical shape, and when the anvil head 110 and the rear head 120 are coupled, as shown in FIG. 4A, the anvil head 110 is formed in a flat egg shape, that is, a relatively elongated shape as compared with a perfectly spherical shape. Thus, when the anvil head 110 is inserted into an intestine, smooth insertion can be guided. The staple accommodation holes 122 are formed in a groove shape such that the staples 124 may be inserted into the bottom inner circumferential surface 121 in a circumferential direction of the bottom inner circumferential surface 121 and in different radial directions. In the present invention, the groove shape of the staple accommodation hole 122 is formed to be approximately flat but is not limited thereto. The staple 124 may be fired according to the operation of an operation button (not shown) provided on the handle part 130 to anastomose a desired position. When an operator operates the operation button (not shown) provided on the handle part 130, the staple 124 protrudes from the staple accommodation hole 122, and a leg of the staple 124 is bent inward by the bottom inner circumferential surface 111 of the anvil head 110 corresponding to the anvil, thereby fixedly joining both organs.

The rear head 120 may include a coupling groove 125 that may be coupled to the coupling guide 112 by guiding the coupling guide 112 of the anvil head 110 to be inserted into the bottom inner circumferential surface 121. Through a coupling between the coupling guide 112 of the anvil head 110 and the coupling groove 125 of the rear head 120, the anvil head 110 and the rear head 120 may be coupled without being misaligned with each other. The trocar 127 that may be fired to protrude through the operation of the handle part 130 may be provided inside the coupling groove 125. Unlike a related art, in the present invention, the trocar 127 does not protrude from the coupling groove 125 before being fired, and thus when the rear head 120 is inserted into an intestine, it is possible to reduce a risk of damaging the intestine. The trocar 127, which is fired to protrude, may enter the trocar accommodation groove 113 of the anvil head 110 so that the anvil head 110 and the rear head 120 may be more strongly coupled as compared with a case in which the anvil head 110 and the rear head 120 are coupled through a magnetic. That is, a coupling between the anvil head 110 and the rear head 120 through the magnet may be regarded as a temporary coupling, and a coupling between the anvil head 110 and the rear head 120 through the trocar accommodation groove 113 and the trocar 127 may be regarded as a main coupling. In addition, since the trocar 127, which is fired to protrude, cannot enter the trocar accommodation groove 113 of the anvil head 110 when the anvil head 110 and the rear head 120 are misaligned with each other, it is important that the anvil head 110 and the rear head 120 are coupled through a coupling between the coupling guide 112 of the anvil head 110 and the coupling groove 125 of the rear head 120 so as not to be misaligned with each other. The bottom inner circumferential surface 121 of the rear head 120 may be provided with a magnet, and the magnet may be formed as a neodymium magnet. The magnet may be formed as an electromagnet, and when the electromagnet needs to be attached to or detached from the rear head 120 in an intestine, magnetism may be imparted to or released from the electromagnet. The magnet may be formed in a donut shape and fixed to the bottom inner circumferential surface 121, but a shape thereof is not limited to the donut shape, and a plurality of magnets may be arranged at equal intervals in a circumferential direction. Furthermore, the rear head 120 may include a cutting tool 126. The cutting tool 126 extends upward in a circumferential direction of the coupling groove 125. When the anvil head 110 and the rear head 120 are coupled, as the coupling guide 112 is inserted into the coupling groove 125, the cutting tool 126 may cut an unnecessary organ part inside a part to be fixed with the staple 124. Furthermore, since the cut organ part is accommodated and protected in the coupling groove 125, a separate processing process for processing cut tissue is not performed. In addition, preferably, a cutting tool groove 117 for separating the bottom inner circumferential surface 111 of the anvil head 110 and the coupling guide 112 is formed in the anvil head 110 such that the cutting tool 126 at least partially enters therein to cut tissue.

As described above, since the bottom inner circumferential surfaces 111 and 121 of the anvil head 110 and the rear head 120 are each provided with the magnet, inside an intestine, the anvil head 110 and the rear head 120 can induce a strong coupling to each other automatically through a magnetic force without additional measures for coupling the anvil head 110 and the rear head 120 to each other at a close position. However, the coupling through the magnet is a temporary coupling as described above, and when a sufficient coupling force is not formed by the temporary coupling, a main coupling through the trocar may be made.

Figure 6:
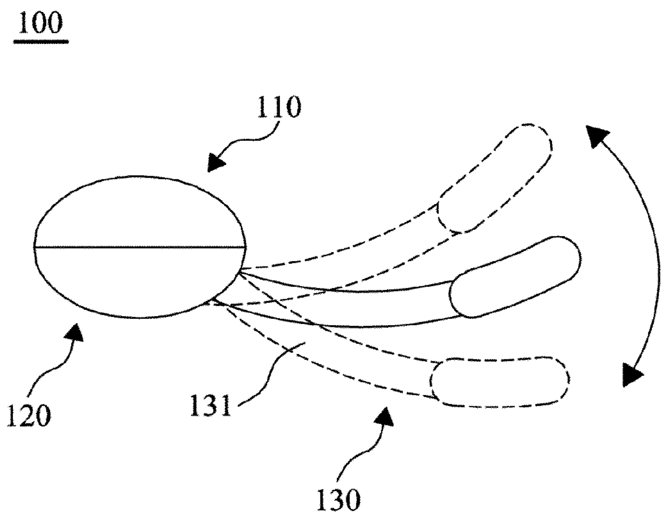
FIG. 6 is a view illustrating an example of a rotation structure of a handle part connected to the rear head of the egg-shaped stapler for intestinal anastomosis according to the present invention.

FIG. 6 is a view illustrating an example of a rotation structure of the handle part connected to the rear head of the egg-shaped stapler for intestinal anastomosis according to the present invention.

The handle part 130 has one end portion coupled to the rear head 120 and the other end portion extending in a rear direction and serves to operate at least one of the anvil head 110 and the rear head 120. The handle part 130 may be rotatably coupled to the rear head 120 to change a position and angle of the egg-shaped stapler 100 according to an anastomotic position of an intestine when the egg-shaped stapler 100 is inserted into the intestine. In particular, since a connector 131 of the handle part 130 has a curved shape rather than a straight line shape unlike a related art, in particular, it is easy for the handle part 130 to be disposed to be inclined at a certain angle in a state in which the anvil head 110 is inserted into an intestine. Although not shown in the present invention, the handle part 130 may include an operation button for firing the staple 124, a staple driving shaft for firing the staple 124, and a connection bar for connecting the operation button and the staple driving shaft, and a detailed description of a structure provided in the handle part 130 to fire the staple 124 will be omitted.

Figure 7:
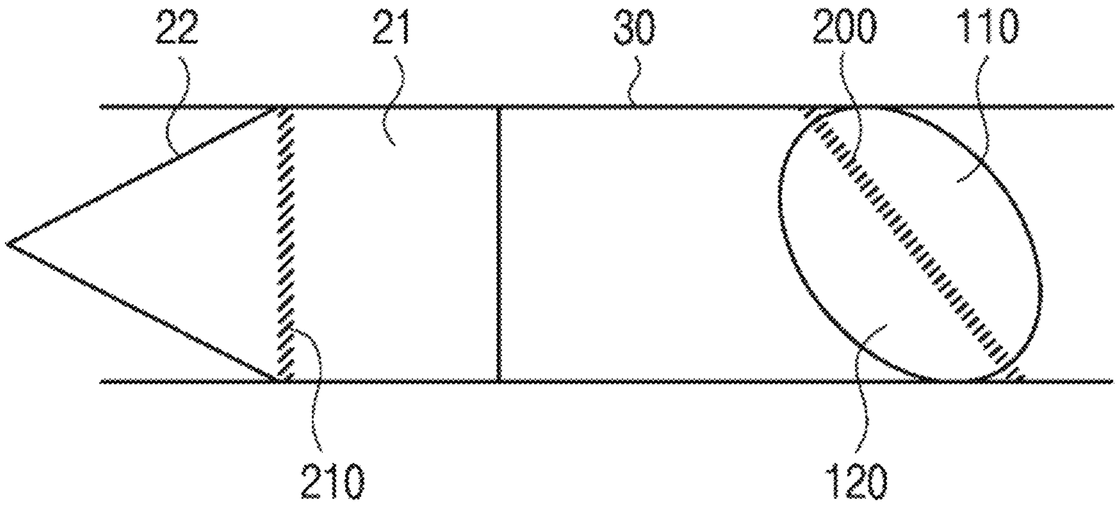
FIG. 7 is a view illustrating an example of comparing an anastomosis shape of the present invention and a conventional anastomosis shape.

FIG. 7 is a view illustrating an example of comparing an anastomosis shape of the present invention and a conventional anastomosis shape.

Since the bottom inner circumferential surfaces 111 and 121 of the anvil head 110 and the rear head 120, which are in contact with each other, are formed in an oval shape, as described above, the bottom inner circumferential surfaces 111 and 121 in contact with each other are formed in an oval shape having a diameter that is relatively greater than an inner diameter of an intestine. Thus, even when the inner diameter of the intestine is small, it is possible to enlarge an area of an inner diameter of an anastomosis part formed after suturing. Referring to FIG. 7, a comparison between an anastomosis shape of a conventional circular stapler and an anastomosis shape of the stapler according to the present invention are briefly shown, when anastomosis is performed in a state in which, after the oval-shaped anvil head 110 and rear head 120 according to the present invention are inserted into an intestine, the anvil head 110 and rear head 120 are inclined at a certain angle, an anastomosis shape 200 is an oval shape inclined at a certain angle, and thus is not irrespective of a size of an inner diameter of the intestine. Furthermore, after intestinal anastomosis, it is possible to guide intestinal anastomosis to be performed to have an inner diameter that is greater than that of a circular anastomosis shape 210 formed by inserting the conventional circular anvil head 22 and rear head 21 in a state perpendicular to a circular cross-section of an intestine 30.

Hereinafter, various embodiments of the present invention will be described.

(1) In an egg-shaped stapler for intestinal anastomosis, which sutures an intestine, the egg-shaped stapler for intestinal anastomosis includes an anvil head which has a bottom inner circumferential surface having an oval shape, a rear head which has a bottom inner circumferential surface having an oval shape in contact with the bottom inner circumferential surface of the anvil head and includes staple accommodation holes capable of accommodating staples along the oval bottom inner circumferential surface, and a handle part which has one end portion coupled to the rear head and the other end portion extending in a rear direction and operates at least one of the anvil head and the rear head.

(2) A surface of the anvil head opposite to the bottom inner circumferential surface is formed in a flat hemispherical shape, a surface of the rear head opposite to the bottom inner circumferential surface of the rear head has a flat hemispherical shape, and the anvil head and the rear head form an egg shape when coupled to each other.

(3) The bottom inner circumferential surface of the anvil head and the bottom inner circumferential surface of the rear head include magnets.

(4) The magnet is formed as an electromagnet.

(5) The anvil head includes a coupling guide protruding from the bottom inner circumferential surface inside the bottom inner circumferential surface of the anvil head, and the rear head includes a coupling groove coupled to the coupling guide.

(6) The anvil head includes a trocar accommodation groove inside the coupling guide.

(7) The egg-shaped stapler includes a trocar accommodated in the trocar accommodation groove, and the trocar does not protrude from the coupling groove before being operated by the handle part.

(8) The bottom inner circumferential surface of the anvil head and the bottom inner circumferential surface of the rear head include magnets, and the anvil head and the rear head are temporarily coupled through the magnets of the bottom inner circumferential surface of the anvil head and the bottom inner circumferential surface of the rear head, and the trocar is accommodated in the trocar accommodation groove so that the anvil head and the rear head are coupled through a main coupling.

(9) The handle part includes a curved connector, and the handle part is rotatably connected to the rear head.

(10) The rear head includes a cutting tool, and the anvil head includes a cutting tool groove into which at least a portion of the cutting tool enters.

In an egg-shaped stapler for intestinal anastomosis according to the present invention, in a state in which an anvil head is first inserted into an intestine, a rear head can be inserted to be accurately and conveniently coupled through a magnet.

In an egg-shaped stapler for intestinal anastomosis according to the present invention, since an anvil head is formed in an egg-like shape in an insertion direction in an intestine, the anvil head can be easily inserted into the intestine.

In an egg-shaped stapler for intestinal anastomosis according to the present invention, an anvil is an egg-like oval anvil head, and irrespective of a size of an inner diameter of an intestine, intestinal anastomosis, which has a larger inner diameter than a perfect circle after the intestinal anastomosis, is possible, thereby reducing a possibility of stenosis of an intestinal anastomosis part after surgery. That is, according to the present invention, since contact surfaces of an anvil head and a rear head are formed in an oval shape having a diameter that is relatively greater than an inner diameter of an intestine, even when the inner diameter of the intestine is small, it is possible to enlarge an area of an inner diameter of an anastomosis part formed after suturing.

By removing an anvil shaft and a trocar that are provided in an anvil head and a rear head of a conventional circular stapler, intestinal insertion can be simplified. In particular, as compared with a straight coupling between a pointed anvil shaft with a narrow cross section and a trocar in a conventional circular stapler, a flat coupling guide with a wide cross section and a coupling groove can be coupled even when the flat coupling guide and the coupling groove are slightly out of a straight line. Furthermore, after an anvil head and a rear head are temporarily coupled through magnets provided on inner circumferential surfaces of both the anvil head and the rear head, before anastomosis, the anvil head and the rear head are coupled through a main coupling using a trocar accommodation groove and a trocar to then form anastomosis, thereby reducing a difficulty of the anastomosis while ensuring the safety of surgery.

The effects of the present invention are not limited to those described above and other effects not described herein will be clearly understood by those skilled in the art from the description in the claims.

The invention claimed is:

1. An egg-shaped stapler for intestinal anastomosis, comprising:

an anvil head having a first bottom inner circumferential surface having an oval shape;

a rear head having a second bottom inner circumferential surface having an oval shape and configured to contact the first bottom inner circumferential surface of the anvil head, the rear head including staple accommodation holes configured to accommodate staples along the second bottom inner circumferential surface; and a handle part having a first end portion coupled to the rear head and a second end portion extending in a rear direction, the handle part being configured to actuate at least one of the anvil head and the rear head, wherein the anvil head includes a coupling guide protruding from the first bottom inner circumferential surface inside the first bottom inner circumferential surface of the anvil head, and a trocar accommodation groove provided inside the coupling guide, wherein the coupling guide is formed as a flat member with a wide cross section protruding from the first bottom inner circumferential surface, wherein the rear head includes a coupling groove configured to receive the coupling guide, and a trocar disposed in the coupling groove, the coupling guide and the coupling groove being configured to align the anvil head and the rear head so as to prevent misalignment between the anvil head and the rear head, and the trocar accommodation groove and the trocar being configured such that, in an aligned state of the anvil head and the rear head, receipt of the trocar in the trocar accommodation groove provides a main coupling between the anvil head and the rear head, wherein the first bottom inner circumferential surface of the anvil head and the second bottom inner circumferential surface of the rear head include magnets configured to temporarily couple the anvil head and the rear head to each other, wherein the trocar is movably disposed in the coupling groove and is configured to move, upon actuation of the handle part, from a non-protruding position accommodated within the coupling groove to a protruding position in which the trocar is received in the trocar accommodation groove, such that the anvil head and the rear head are coupled to each other, wherein the rear head further includes a cutting tool extending upward along a circumferential direction of the coupling groove, wherein the anvil head further includes a cutting tool groove formed between the first bottom inner circumferential surface and the coupling guide and configured to receive at least a portion of the cutting tool, wherein the cutting tool and the cutting tool groove are configured such that an unnecessary organ portion located inside a portion to be fixed by the staples is cut, and the cut unnecessary organ portion is received in the coupling groove.

2. The egg-shaped stapler of claim 1, wherein:

a surface of the anvil head opposite to the first bottom inner circumferential surface is formed in a flat hemispherical shape;

a surface of the rear head opposite to the second bottom inner circumferential surface of the rear head has a flat hemispherical shape; and the anvil head and the rear head form an egg shape when coupled to each other.

3. The egg-shaped stapler of claim 1, wherein the magnets are electromagnets.

4. The egg-shaped stapler of claim 1, wherein the handle part includes a curved connector and is rotatably connected to the rear head.

* * * * *